United States Patent [19]
Ronan et al.

[11] Patent Number: 5,820,918
[45] Date of Patent: Oct. 13, 1998

[54] MEDICAL DEVICES CONTAINING IN-SITU GENERATED MEDICAL COMPOUNDS

[75] Inventors: John M. Ronan; Samuel A. Thompson, both of New Castle, Del.

[73] Assignee: Hercules Incorporated, Wilmington, Del.

[21] Appl. No.: 679,608

[22] Filed: Jul. 11, 1996

[51] Int. Cl.$^6$ .............................. A61M 25/00; B05D 1/18; B05D 7/24; B05D 1/36

[52] U.S. Cl. ........................ 427/2.1; 427/2.25; 427/2.3; 427/343; 427/419.8; 623/1; 623/12; 606/192; 606/198; 604/8; 604/96; 604/265; 600/29; 600/36; 424/423; 424/445; 424/617; 424/619; 424/630

[58] Field of Search ...................... 128/898; 427/2.25, 427/2.3, 2.31, 2.28, 343, 353, 419.8, 2.13, 430.1; 424/423, 445, 617, 619, 630; 623/1, 12; 604/8, 304, 96, 265; 606/192, 154, 198; 600/29, 36

[56] References Cited

U.S. PATENT DOCUMENTS

| | | | |
|---|---|---|---|
| 2,689,809 | 9/1954 | Fessler . | |
| 2,791,518 | 5/1957 | Stokes, Jr. et al. | 427/2.31 |
| 3,975,350 | 8/1976 | Hudgin et al. | 260/30.4 N |
| 4,265,927 | 5/1981 | Ericksson et al. | 427/2.3 |
| 4,286,341 | 9/1981 | Greer et al. | 3/1.4 |
| 4,366,183 | 12/1982 | Grommidh et al. | 427/2.27 |
| 4,527,293 | 7/1985 | Eckstein et al. | 623/12 |
| 4,548,844 | 10/1985 | Podell et al. | 427/322 |
| 4,592,920 | 6/1986 | Murtfeldt | 427/2.25 |
| 4,878,907 | 11/1989 | Okada et al. | 623/1 |
| 4,941,870 | 7/1990 | Okada et al. | 427/2.25 |
| 4,948,575 | 8/1990 | Cole et al. | 424/44 |
| 4,981,487 | 1/1991 | da Costa | 8/507 |
| 5,057,606 | 10/1991 | Garbe | 536/54 |
| 5,085,629 | 2/1992 | Goldberg et al. | 604/8 |
| 5,234,456 | 8/1993 | Silvestrini | 606/194 |
| 5,531,716 | 7/1996 | Luzio et al. | 604/264 |
| 5,531,735 | 7/1996 | Thompson | 604/891.1 |
| 5,541,304 | 7/1996 | Thompson | 536/20 |
| 5,607,683 | 3/1997 | Capelli | 424/404 |
| 5,674,521 | 10/1997 | Gehrke et al. | 424/423 |
| 5,684,051 | 11/1997 | Thompson | 514/777 |

FOREIGN PATENT DOCUMENTS

| | | |
|---|---|---|
| 0507604A-2 | 4/1992 | European Pat. Off. . |
| 0645150A-1 | 9/1994 | European Pat. Off. . |

*Primary Examiner*—Diana Dudash
*Attorney, Agent, or Firm*—Martin F. Sloan

[57] ABSTRACT

A process for impregnating a medical device made from a water absorbable polymer material, e.g., a hydrogel, with a medical compound having low solubility in aqueous solutions, e.g., an antiseptic or radiopaque compound, is disclosed. The device is first infiltrated with an aqueous solution containing a first water soluble, ionizable compound, and subsequently infiltrated with an aqueous solution containing a second water soluble, ionizable compound. The ionizable compounds are selected such that they react after mutual contact to form the medical compound in-situ within the device.

52 Claims, No Drawings

5,820,918

MEDICAL DEVICES CONTAINING IN-SITU GENERATED MEDICAL COMPOUNDS

BACKGROUND OF THE INVENTION

1. Field of the Invention

The invention relates to medical devices containing in-situ generated medical compounds and to a method for preparing same.

2. Description of Related Art

Medical devices adapted for implant into the body to facilitate the flow of bodily fluids, to serve as vascular grafts or for other purposes have been developed. Typically, these devices include stents, catheters or cannulas, plugs, constrictors, tissue or biological encapsulants and the like.

Many of these devices used as implants are made of durable, non-degradable plastic materials such as polyurethanes, polyacrylates, silicon polymers and the like, or more preferably from biodegradable polymers which remain stable in-vivo for a period of time but eventually biodegrade in-vivo into small molecules which are removed by the body by normal elimination in urine or feces.

Typical of such biodegradable polymers include polyesters, polyanhydrides and polyorthoesters which undergo hydrolytic chain cleavage, as disclosed in U.S. Pat. No. 5,085,629; crosslinked polysaccharide hydrogel polymers as disclosed in EPA 0507604 A-2 and U.S. Pat. No. 5,057,606 and other ionically crosslinked hydrogels as disclosed in U.S. Pat. Nos. 4,941,870, 4,286,341 and 4,878,907.

EPA 0645150 A-1 describes hydrogel medical devices prepared from anionic polymers, e.g., polysaccharides such as calcium alginate or ionically crosslinked cationic polymers such as chitosan, cationic guar, cationic starch and polyethylene amine. These devices are adapted for in-vivo disintegration upon the administration of a chemical trigger material which displaces crosslinking ions.

It is often desirable to include in the formulation of such degradable or non-degradable polymer materials one or more medical compounds which have antibacterial and/or antiseptic properties or which impart radiopacity to the medical device, i.e., allow the device to be observed in-vivo by x-ray radiography. Examples of excellent antiseptic agents include silver chloride, carbonate or citrate; suitable radiopaques include barium salts such as barium sulfate and bismuth salts such as bismuth subcarbonate. Ideally, such additives have relatively low water solubility to prevent their being rapidly washed away by body fluids.

However, in many cases, these polymer compositions can not be easily manufactured due to the relative water insolubility of the medical compound additive which is to be formulated into the polymer composition, usually in an aqueous polymer medium. Formulation problems typically stem from process limitations such as viscosity (too high to mix or too low to suspend particulate fillers), thermal sensitivity of the additives to extrusion or molding process conditions used to shape the medical device, viscosity of the additives, solubility of the additives and the like.

One method used to prepare radiopaque medical devices based on polymers which are cationic salts of anionic polymers, e.g., calcium alginate, is to exchange at least a portion of the calcium ions with one or more radiopaque ions such as barium ions, as taught in commonly owned copending U.S. patent application Ser. No. 08/566,452, filed Dec. 1, 1995, the complete disclosure which is incorporated herein by reference. Such an approach may, however, introduce variables which can affect the strength and/or biodegradation properties of the treated medical device.

SUMMARY OF THE INVENTION

The present invention provides polymeric medical devices such as implants which are impregnated with a medical compound having low water solubility such as an antiseptic compound or a radiopaque compound, wherein said medical compound is formed in-situ from at least two water soluble constituents thereof.

The invention also provides a process for impregnating a medical device comprising a water absorbable polymer material with a medical compound having low water solubility comprising: a) contacting at least a portion of said device with a first aqueous solution containing a first water soluble ionizable compound dissolved therein such that the contacted portion of said device is infiltrated by said first aqueous solution; b) contacting said portion of said device with a second aqueous solution containing a second water soluble ionizable compound dissolved therein such that said contacted portion of said device is also infiltrated by said second aqueous solution; said water soluble compounds characterized by the fact that the ions thereof react after contact to form said medical compound having low water solubility within said device.

DETAILED DESCRIPTION OF THE INVENTION

Suitable polymer materials which may be used to fabricate the medical devices of this invention are either non-porous materials which are capable of swelling in and absorbing aqueous solutions such that the aqueous solution can infiltrate the polymer matrix, or porous polymer structures which permit infiltration of the aqueous solution through the pores. Examples of polymer materials which may be used include natural or synthetic polymers or copolymers. The polymer may be an ionically or covalently crosslinked hydrogel, or a non-crosslinked material.

The ionically crosslinkable polymers from which the medical device may be fabricated may be anionic or cationic in nature and may include but are not limited to carboxylic, sulfate, and amine functionalized polymers. Suitable such polymers include polyacrylic acid, polymethacrylic acid, polyethylene amine, polysaccharides such as alginic acid, pectinic acid, carboxymethyl cellulose, hyaluronic acid, heparin, chitosan, carboxymethyl chitosan, carboxymethyl starch, carboxymethyl dextran, heparin sulfate, chondroitin sulfate, cationic guar, cationic starch, and their salts. Preferred ionically crosslinkable polymers are alginic acid, pectinic acid, carboxymethyl cellulose, hyaluronic acid, chitosan, and their salts. Most preferred ionically crosslinkable polymers are alginic acid, pectinic acid, and hyaluronic acid and their salts. Among the ionically crosslinkable cationic polymers that may be employed are chitosan, cationic guar, cationic starch and polyethylene amine.

The crosslinking ions may be anions or cations. Appropriate crosslinking ions include but are not limited to cations comprising an ion selected from the group consisting of calcium, magnesium, barium, strontium, boron, beryllium, aluminum, iron, copper, cobalt, lead and silver ions. Anions may be selected from the group consisting of phosphate, citrate, borate, succinate, maleate, adipate and oxalate ions. More broadly, the anions are derived from polybasic organic or inorganic acids. Preferred crosslinking cations are calcium, iron, and barium ions. The most preferred crosslinking cations are calcium and barium ions. The most preferred crosslinking anion is phosphate.

Other polymers from which the medical device may be fabricated include non-crosslinked polymers which may or may not be subject to polymer chain degradation or accelerated hydrolysis when contacted with an enzyme or an acid or base. Examples of such polymers include polyesters such as polylactides, polyglycolides, polyhydroxy butyric acid, polyhydroxy valeric acid, polycaprolactone and lactone copolymers; polyanhydrides; polyorthoesters; poly-amino acids; poly(meth) acrylic acids; polyvinylalcohol; polyoxymethylene and like materials. These materials may also be ionically or covalently crosslinked.

The biodegradable hydrogel polymers are selected such that they are essentially insoluble or only very slowly soluble in typical body fluids with which they will come in contact, e.g., urine, blood, bile, feces or intestinal fluids, but will become dispersed or dissolved in such fluids after a period of time or after contact with an appropriate disintegration triggering agent. The term "hydrogel" indicates a crosslinked, water insoluble, water-containing material.

As described above, polymers forming all or a portion of the medical device are either porous materials or relatively non-porous materials. Water and small ionizable molecules dissolved in the water will, in either case, be able to penetrate into the polymer matrix through various mechanisms, including diffusion.

The process of the invention for the in-situ generation of a medical compound within the polymer matrix or pore structure of a medical device comprises an initial infiltration of the device with an aqueous solution containing a first water soluble ionizable compound, followed by infiltration of a second aqueous solution containing a second water soluble ionizable compound. The ionizable compounds may be organic or inorganic acids, bases or salts, but salts are preferred. When ions of the first solution encounter ions of the second solution, a reaction, including salt exchange, takes place such that the desired medical compound having low water solubility is precipitated within the medical device.

The term "medical compound" is defined for the purposes of this invention to include but is not limited to filler for mechanical reinforcement, filler for toughening, filler for increased radiopacity, filler for flame retardancy, filler or dye for coloration, medically active agents such as antiseptics, antibiotics, drugs, coagulants, anticoagulants, and anti-inflammatory agents. The infiltrated salts of this invention are soluble in the infiltration solutions. The deposited compounds are of low solubility in the infiltration solutions. Most preferably the deposited compounds are substantially insoluble in the infiltration solutions.

The preferred infiltration solutions contain salts dissolved therein. The salt ions may be mono- or poly valent, inorganic, organic or both. Ions are selected based on the function of the medical compound desired to be deposited in the medical device, the known solubility of the in-organic and organic salts used in the infiltration solutions and the product generated within the medical device after reaction of the infiltration salt ions.

In general, the infiltration salts are selected based on the following criteria:

a) they must be water soluble, i.e., a solubility at room temperature in aqueous solution of at least about 0.1 gr/liter, more preferably at least about 1.0 gr/liter and most preferably at least about 5 g/liter;

b) the salt ions of the first and second solutions should be selected such that a reaction (ion exchange) will occur when these ions contact one another to yield appreciable amounts of a precipitate which imparts the desired properties to the medical device as discussed above; and c) the resulting precipitate (medical compound) formed in-situ must have low water solubility, i.e., a solubility in aqueous solution at room temperature of less than about 0.5 gr/liter, more preferably less than about 0.1 gr/liter, and most preferably less than about 0.05 gr/liter.

Suitable combinations of a few infiltration salts and their reaction products are shown in Table 1. Other combinations can be readily determined by one skilled in the art.

TABLE 1

| SALT 1 | SALT 2 | INSOLUBLE REACTION PROD. | FUNCTION |
|---|---|---|---|
| $CH_3COOAg$ | $CaCl_2.2H_2O$ | AgCl | Antiseptic |
| $Na_2SO_4$ | $BaCl_2.2H_2O$ | $BaSO_4$ | Radiopaque |

For example, if the desired function is to make a device radiopaque, then first a heavy metal compound is selected from the typical list of radiopacifiers used in industry (barium sulfate, bismuth subcarbonate). If barium sulfate is selected, the CRC handbook of solubilities is consulted. Barium chloride dihydrate is very soluble in water (>30 gr/100 gr cold water, 58.7 gr/100 gr hot water) and would be a good choice for the first infiltration salt. Sodium sulfate heptahydrate is also very water soluble (19.5 gr/100 gr cold water, 44 gr/100 gr hot water) and would make an excellent choice for the second infiltration salt. Sequential infiltration would lead to the precipitation of barium sulfate (solubility of 0.000222 gr/100 gr cold water, 0.000336 gr/100 gr hot water) inside the device.

Preferred heavy metal compounds for use in radiopaque applications include compounds, e.g., salts, of a metal having an atomic weight of greater than about 40, preferably greater than about 50. Suitable metals include barium, strontium, iron, copper, lead, tin, zinc, gold, silver, bismuth and manganese.

If the desired function is to provide an antiseptic agent, then first a list of known antiseptics is consulted. Silver ions are an effective antiseptic. Controlled release of silver ions from a medical device or medical device coating can be accomplished with the use of a silver salt having low solubility in water. To deposit an antiseptic inside an article, the article is immersed in an aqueous solution of silver acetate (solubility 1.02 g/liter cold water, 2.52 g/liter hot water). Silver acetate diffuses into the article. The infiltrated article, which now contains silver acetate, is then immersed into an electrolyte solution containing an anion which will form a silver salt having lower solubility in water than silver acetate. Examples of appropriate counter-anions include: chloride (AgCl solubility of 0.000089 g/liter water), carbonate ($Ag_2CO_3$ solubility of 0.0032 g/liter), citrate (solubility of 0.028 g/liter), iodide (solubility of $2.8 \times 10^{-7}$ g/liter), and nitrite (solubility of 0.155 g/liter).

In both cases, the barium or silver compounds will precipitate out inside the device in the form of fine crystalline solids. The subsequent release rate of the highly water insoluble precipitate from the device will be dictated by the environment of the device (in-vivo body fluids and temperature encountered by the device), precipitate solubility, particle size, ionic strength of surrounding medium, diffusion (surface area/volume) and loading level of the precipitate within the device.

Infiltration is defined to include swelling as well as the penetration of pores and channels in the article. Infiltration may be complete, or infiltration may be limited to areas within the article as desired, e.g., interior coatings in hollow tubular devices. The level of medical compound which is deposited in the article will be a function of the amount of solution infiltrated into the article, the concentration of the ions in the first and second infiltration solutions, the solubility of the precipitated compound in the infiltration solutions, and the number of infiltration cycles used. Infiltration conditions can be adjusted such that deposition occurs primarily in selected areas such as inside coatings, in surface or subsurface layers of the article, or in the core of the article. In general, infiltration conditions are selected such that the quantity of precipitate (medical compound) deposited within the device is in the range of from about 0.001 to about 50 wt %, based on the weight of the device, more preferably from about 0.01 to about 15 wt %. Where the medical compound is a radiopaque filler, the preferred range is from about 5 to about 15 wt %. Where the medical compound is an antiseptic, the preferred range is from about 0.01 to about 5 wt %.

The infiltration solutions used in accordance with this invention are aqueous solutions which may also contain up to about 50 volume % of other water miscible solvents such as alcohols, glycols, ether and ester solvents. The solutions may also contain wetting agents, dispersants, anticoagulants and supplemental medicines or medical compounds.

Medical devices which may be fabricated in accordance with this invention include films, stents, catheter or cannulas, plugs and constrictors, for both human and animal use. The invention is particularly applicable to medical stents of tubular configuration which come in contact with one or more body fluids such as blood, urine, gastrointestinal fluids, and bile. The devices are particularly applicable for use in gastrointestinal, urogenital, cardiovascular, lymphatic, otorhinolaryngo-logical, optical, neurological, integument and muscular body systems.

Linear device or pre-device shaped configurations such as fibers, rods, tubes or ribbons can be manufactured in accordance with the present invention by using a spinning device in which a solution of an ionically crosslinkable matrix polymer is forced through a shaping die into a crosslinking bath containing the crosslinking ions. If the ionically crosslinkable polymer solution is aqueous, the product after crosslinking is typically described as a hydrogel. The hydrogel may be used as made or further given a three dimensional shape through treatment in a crosslinking solution after being forced into the desired shape. After equilibration, the hydrogel will retain the new three dimensional shape. The device may be used in its hydrogel form or in a dehydrated form. During dehydration the three dimensional shape is retained.

Another process for manufacturing the articles of the present invention comprises introducing a solution comprising ionically crosslinkable polymer through a die to form a tube, simultaneously pumping a solution comprising crosslinking ion through the formed tube, and extruding the formed tube from said die into a solution comprising crosslinking ion. In this process the crosslinking step may involve shaping of the device as in wet spinning of a tubular device. Alternatively, the device may be prepared by molding a latent crosslinking composition using a one or two part reaction injection molding system. The term "tubular" as used herein, includes not only cylindrical shaped devices having circular cross sections, but also devices having different cross sections as long as such articles have a hollow passageway which distinguishes a tube from a rod.

Another process for the manufacture of the devices of the present invention would be conventional molding techniques such as reaction injection molding wherein the ionically crosslinkable polymer and the crosslinking ion are mixed and introduced into a mold to form an article of the desired configuration.

More complex shaped devices can be made using a one or two part reaction injection molding composition. These molding compositions typically contain the ionically crosslinkable polymer in solution, the crosslinking ion in an insoluble or slowly soluble form and additives to cause dissolution of the crosslinking ion. When the crosslinking ion dissolves and dissociates, the ionically crosslinkable polymer solution gels. This gel (or hydrogel if the solvent is water) may be used as made or further developed, crosslinked and shaped by soaking in a solution of a crosslinking ion. Dissolution of the crosslinking ion to form the gel may be effected by using a two part molding system in which the second component contains an acid or pre-acid such as a cyclic lactone which lowers the pH and solubilizes the previously insoluble crosslinking ion.

Where the matrix polymer is non ionic, the device can be prepared by spinning or extruding a solution or melt of the polymer composition into a liquid bath and collecting the resultant shaped article.

The medical devices may be infiltrated with the solutions of this invention by contacting the device or a portion thereof with the solution for a period of time sufficient for the device to absorb appreciable quantities of the solution. Where the device is hydrogel, it may be partially dried prior to contact with one or both solutions to facilitate increased solution absorption. This contact may be repeated one or more times in order to increase the level of infiltrate in the device, and the device may be washed and partially dried between each infiltration cycle. The device may be totally or partially immersed in the respective solutions. Devices in the shape annular tubular cylinders may be selectively infiltrated by sequentially flowing solutions only through the inner annular portion, or only over the outer circumference of the tube. The device may be subsequently washed or soaked in distilled water to remove residual ions, and the solvent, e.g., water, may be removed from the device after completion of the deposition process.

The following examples are illustrative of the invention.

Examples 1 and 2 detail the preparation of calcium alginate and barium alginate hydrogel tubings which are subsequently infiltrated with representative medical compounds in accordance with example 3–6.

EXAMPLE 1

Preparation of Calcium Hydrogel Tubing 120.45 grams of Pronova Protanal LF 10/60 sodium alginate were mixed into 629.63 grams of deionized water. The sample was stirred for about ten seconds, and was then stored at room temperature overnight. This mixture sample was mixed in a Ross double planetary mixer at 60° C. for 60 minutes. The mixture was then allowed to cool to 30° C. in the mixer. The mixture was then loaded into sterile 30 cc syringes which were then centrifuged to remove entrapped air.

These syringes were attached to a tubing die, powered with a syringe pump, and tubing was extruded into a 10% calcium chloride dihydrate solution. The calcium solution was also pumped through the center of the die as the tube was extruded. The tubing was left in the calcium solution overnight. The following day the tubing was dialyzed in deionized water to remove excess ions.

EXAMPLE 2

Preparation of Barium Alginate Hydrogel Tubing

Calcium alginate hydrogel tubing prepared as in example 1 was soaked in an aqueous 25% potassium chloride solution for forty minutes, with stirring, to strip the calcium ions. Then the tubing was soaked for one hour in an aqueous 2.5% $BaCl_2.2H_2O$ solution with constant mixing. The tubes were then placed into deionized water for thirty minutes. The water was poured out and was replaced with fresh deionized water. Thirty minutes later the water was changed again. Thirty minutes later, the water was replaced with 3000 grams of an aqueous 0.15% sodium sulfate solution in water. After ten minutes in the $Na_2SO_4$ solution, the solution was poured out and was replaced with fresh DI water. The DI water was refreshed after thirty minutes and then again thirty minutes later. The barium alginate tubing was stored in deionized water.

In examples 3 and 4, the tubings prepared in examples 1 and 2 were impregnated with an antiseptic agent (AgCl).

EXAMPLE 3

Calcium alginate hydrogel tubing prepared as in example 1 above was soaked in an aqueous 1% silver acetate solution for one hour and then was soaked in an aqueous 30% $CaCl_2.2H_2O$ for one hour. A second sample of calcium alginate tubing (control) was soaked only in the aqueous 30% $CaCl_2.2H_2O$. The samples were dried under vacuum at 60° C. The solids were then analyzed by spectroscopy for Ca and Ag. The % solids is reported below.

|  | Solids | Spectroscopy |
| --- | --- | --- |
| Ag Treated | 31.8 ± .5% | 6.43% Ca |
|  |  | 18.7% Ag |
| Control | 23.9 ± .3% | 8.43% Ca |

EXAMPLE 4

Barium alginate hydrogel tubing prepared as in example 2 above was soaked in an aqueous 1% silver acetate solution for one hour followed by a one hour soak in an aqueous 2.5% $BaCl_2.2H_2O$ solution. A second sample (control) of barium alginate tubing was soaked for one hour only in the aqueous 2.5% $BaCl_2.2H_2O$ solution. The samples were dried under vacuum at 60° C. to determine the solids level. The solids were then analyzed by spectroscopy for Ba and Ag.

|  | Solids | Spectroscopy |
| --- | --- | --- |
| Ag Treated | 27.0 ± .4% | 20.3% Ba |
| Control | 22.0 ± .2% | 24.3% Ba |

The material prepared according to Example 4 possesses both some radiopaque properties due to the exchange of calcium with barium as in Example 2, and antiseptic properties due to the in-situ formation of AgCl.

In examples 5 and 6, the tubings prepared in examples 1 and 2 were impregnated with a radiopaque agent ($BaSO_4$).

EXAMPLE 5

Calcium alginate tubing prepared as in example 1 above was soaked in an aqueous 15% $Na_2SO_4$ solution for five minutes followed by an overnight soak in an aqueous 2.5% $BaCl_2.2H_2O$ solution. A control sample was run by soaking the calcium alginate tubing only in 2.5% $BaCl_2.2H_2O$ overnight. The samples were dried under vacuum at 60° C. to determine the solids level. The solids were then analyzed by spectroscopy for Ba and Ca.

|  | Solids | Spectroscopy |
| --- | --- | --- |
| $Na_2SO_4$ Treated | 21.6 ± .1% | 28.6% Ba |
|  |  | 0.1% Ca |
| Control | 22.1 ± .4% | 24.7% Ba |
|  |  | 0.15% Ca |

The sodium sulfate treated sample was swollen during the sulfate treatment leading to a higher water content and lower solids level than the control. The barium level is higher as a result of precipitated barium sulfate in the hydrogel.

EXAMPLE 6

Barium alginate hydrogel tubing prepared as in example 2 above was soaked in an aqueous 5% $Na_2SO_4$ solution for five minutes followed by an overnight soak in an aqueous 2.5% $BaCl_2.2H_2O$ solution. A second sample (control) was soaked only in aqueous 2.5% $BaCl_2.2H_2O$ solution for one hour. The samples were dried under vacuum to determine the solids level. The solids were then analyzed by spectroscopy for Ba and Ca.

|  | Solids | Spectroscopy |
| --- | --- | --- |
| $Na_2SO_4$ Treated | 25.3 ± .4% | 33.8% BA |
|  |  | <0.1% Ca |
| Control | 22.0 ± .2% | 24.3% Ba |

Once again, the higher barium level in the test sample reflects precipitated barium sulfate present in the hydrogel.

As can be seen from the above experiments, this invention facilitates mass production of articles with a base formulation which may then later be specialized with the introduction of function-specific additives. The invention is particularly valuable in the medical device field where medically active agents are often degraded by device process conditions such as high temperature and pressure typically used to extrude tubing for stent and catheter manufacture.

What is claimed is:

1. A process for impregnating a medical device comprising a water absorbable polymer material with a medical compound having water solubility less than about 0.5 g/liter comprising:

a) contacting at least a portion of said device with a first aqueous solution containing a first water soluble ionizable compound dissolved therein such that the contacted portion of said device is infiltrated by said first aqueous solution;

b) contacting said portion of said device with a second aqueous solution containing a second water soluble ionizable compound dissolved therein such that the contacted portion of said device is also infiltrated by said second aqueous solution;

said water soluble compounds characterized by the fact that the ions thereof react after contact to form said medical compound having water solubility less than about 0.5 g/liter within said device, said water absorbable polymer material comprising ionically or covalently crosslinked hydrogel; and said medical compound being selected from the group consisting of radiopaque compounds present in said device at a level of from about 5 to about 15 wt % and antiseptic agents present in said device at a level of from about 0.01 to about 5 wt %.

2. The process of claim 1 wherein said water soluble, ionizable compounds are selected from the group consisting of organic or inorganic salts.

3. The process of claim 1 wherein said polymer material comprises a crosslinked ionic polymer hydrogel.

4. The process of claim 3 wherein said crosslinked ionic polymer hydrogel comprises anionic polymer crosslinked with crosslinking cations.

5. The process of claim 4 wherein said anionic polymer is selected from the group consisting of polyacrylic acid, polymethacrylic acid, alginic acid, pectinic acid, carboxyl methyl cellulose, hyaluronic acid, heparin, carboxymethyl starch, carboxymethyl dextran, heparin sulfate, and chondroitin sulfate, and salts thereof.

6. The process of claim 5 wherein said anionic polymer is selected from the group consisting of alginic acid, pectinic acid, carboxymethyl cellulose, hyaluronic acid and salts thereof.

7. The process of claim 4 wherein said crosslinking cations are selected from the group consisting of calcium, magnesium, barium, strontium, boron, beryllium, aluminum, iron, copper, cobalt, lead and silver ions.

8. The process of claim 7 wherein said crosslinking cations are selected from the group consisting of calcium, barium, iron and aluminum ions.

9. The process of claim 3 wherein said crosslinked ionic polymer hydrogel comprises cationic polymer crosslinked with crosslinking anions.

10. The process of claim 9 wherein said crosslinked cationic polymer comprises at least one polymer selected from the group consisting of chitosan, cationic guar, cationic starch and polyethylene amine.

11. The process of claim 9 wherein said crosslinking anions are selected from the group consisting of phosphate, citrate, borate, succinate, maleate, adipate and oxalate ions.

12. The process of claim 1 wherein said medical compound is a radiopaque compound present in said device at a level of from about 5 to about 15 wt %.

13. The process of claim 12 wherein said radiopaque compound contains a metal having an atomic weight of greater than about 40.

14. The process of claim 13 wherein said metal is selected from the group consisting of barium, strontium, iron, copper, lead, tin, zinc, gold, silver, bismuth and manganese.

15. The process of claim 14 wherein said metal is barium.

16. The process of claim 1 wherein the medical compound is an antiseptic agent present in said device at a level of from about 0.01 to about 5 wt %.

17. The process of claim 16 wherein said antiseptic agent contains silver.

18. The process of claim 16 wherein said antiseptic agent is selected from the group consisting of silver chloride, silver carbonate, silver citrate, silver iodide and silver nitrite.

19. The process of claim 1 wherein said first and second water soluble ionizable compounds have a solubility in aqueous solution at room temperature of at least about 0.1 g/liter.

20. The process of claim 19 wherein said solubility is at least about 5 g/liter.

21. The process of claim 19 wherein said medical compound has a solubility in aqueous solution at room temperature of less than about 0.1 g/liter.

22. The process of claim 21 said solubility is less than about 0.05 g/liter.

23. The process of claim 1 wherein said medical device is a pre-shaped medical device.

24. The process of claim 1 wherein said medical device is selected from the group consisting of stents, catheters or cannulas, plugs, constrictors and tissue or biological encapsulants.

25. The process of claim 1 wherein said medical device is contacted with each of said solutions by immersion.

26. The process of claim 1 including the step:
    c) washing said device after step (b) with water to remove excess water soluble ions from said device.

27. An impregnated medical device prepared by the process of claim 1.

28. The device of claim 27 wherein said water soluble, ionizable compounds are selected from the group consisting of organic or inorganic salts.

29. The device of claim 27 wherein said polymer material comprises a crosslinked ionic polymer hydrogel.

30. The device of claim 29 wherein said crosslinked ionic polymer hydrogel comprises anionic polymer crosslinked with crosslinking cations.

31. The device of claim 30 wherein said anionic polymer is selected from the group consisting of polyacrylic acid, polymethacrylic acid, alginic acid, pectinic acid, carboxyl methyl cellulose, hyaluronic acid, heparin, carboxymethyl starch, carboxymethyl dextran, heparin sulfate, and chondroitin sulfate, and salts thereof.

32. The device of claim 31 wherein said anionic polymer is selected from the group consisting of alginic acid, pectinic acid, carboxymethyl cellulose, hyaluronic acid and salts thereof.

33. The device of claim 30 wherein said crosslinking cations are selected from the group consisting of calcium, magnesium, barium, strontium, boron, beryllium, aluminum, iron, copper, cobalt, lead and silver ions.

34. The device of claim 33 wherein said crosslinking cations are selected from the group consisting of calcium, barium, iron and aluminum ions.

35. The device of claim 29 wherein said crosslinked ionic polymer hydrogel comprises cationic polymer crosslinked with crosslinking anions.

36. The device of claim 35 wherein said crosslinked cationic polymer comprises at least one polymer selected from the group consisting of chitosan, cationic guar, cationic starch and polyethylene amine.

37. The device of claim 35 wherein said crosslinking anions are selected from the group consisting of phosphate, citrate, borate, succinate, maleate, adipate and oxalate ions.

38. The device of claim 27 wherein said medical compound is a radiopaque compound present in said device at a level of from about 5 to about 15 wt %.

39. The device of claim 38 wherein said radiopaque compound contains a metal having an atomic weight of greater than about 40.

40. The device of claim 39 wherein said metal is selected from the group consisting of barium, strontium, iron, copper, lead, tin, zinc, gold, silver, bismuth and manganese.

41. The device of claim 40 wherein said metal is barium.

42. The device of claim 27 wherein said medical compound is an antiseptic agent present in said device at a level of from about 0.01 to about 5 wt %.

43. The device of claim 42 wherein said antiseptic agent contains silver.

44. The device of claim 42 wherein said antiseptic agent is selected from the group consisting of silver chloride, silver carbonate, silver citrate, silver iodide and silver nitrite.

45. The device of claim 27 wherein said first and second water soluble ionizable compounds have a solubility in aqueous solution at room temperature of at least about 0.1 g/liter.

46. The device of claim 45 wherein said solubility is at least about 5 g/liter.

47. The device of claim 45 wherein said medical compound has a solubility in aqueous solution at room temperature of less than about 0.1 g/liter.

48. The device of claim 47 said solubility is less than about 0.05 g/liter.

49. The device of claim 27 which is a pre-shaped medical device.

50. The device of claim 27 which is selected from the group consisting of stents, catheters or cannulas, plugs, constrictors and tissue or biological encapsulants.

51. The device of claim 27 which is contacted with each of said solutions by immersion.

52. The device of claim 27 which is prepared by the further step of:

(c) washing said device after step (b) with water to remove excess water soluble ions from said device.

* * * * *